United States Patent
Sakaki et al.

(10) Patent No.: US 8,889,903 B2
(45) Date of Patent: Nov. 18, 2014

(54) SYNTHESIS OF RARE EARTH METAL EXTRACTANT

(75) Inventors: Kazuaki Sakaki, Echizen (JP); Hiroto Sugahara, Echizen (JP); Tetsuya Ohashi, Echizen (JP); Tetsuya Kume, Echizen (JP); Masahiko Ikka, Echizen (JP); Hirochika Naganawa, Ibaraki (JP); Kojiro Shimojo, Ibaraki (JP)

(73) Assignees: Shin-Etsu Chemical Co., Ltd., Tokyo (JP); Nissin Chemical Industry Co., Ltd., Fukui-ken (JP)

( * ) Notice: Subject to any disclaimer, the term of this patent is extended or adjusted under 35 U.S.C. 154(b) by 0 days.

(21) Appl. No.: 13/176,252

(22) Filed: Jul. 5, 2011

(65) Prior Publication Data

US 2012/0004459 A1    Jan. 5, 2012

(30) Foreign Application Priority Data

Jul. 5, 2010   (JP) .................... 2010-153175

(51) Int. Cl.
 *C07C 231/02*   (2006.01)
(52) U.S. Cl.
 CPC ................... *C07C 231/02* (2013.01)
 USPC ........................................ 562/567
(58) Field of Classification Search
 CPC ................. C07C 231/02; C07C 233/16
 See application file for complete search history.

(56) References Cited

U.S. PATENT DOCUMENTS

| | | | | |
|---|---|---|---|---|
| 4,123,538 A | * | 10/1978 | Umen | 514/330 |
| 4,713,446 A | * | 12/1987 | DeVore et al. | 530/356 |
| 2003/0176641 A1 | * | 9/2003 | Gokel et al. | 530/329 |

FOREIGN PATENT DOCUMENTS

| | | | |
|---|---|---|---|
| JP | 2007-327085 A | | 12/2007 |
| JP | 2007327085 A | * | 12/2007 |
| WO | 03/059937 A2 | | 7/2003 |

OTHER PUBLICATIONS

Solomons, Organic Chemistry, 5th Edition, 1992. John Wiley & Son, Inc., New York, pp. 786-788.*

Djedovic, N. et al.; "The C- and N-terminal residues of synthetic heptapeptide ion channels influence transport efficacy through phospholipid bilayers", New Journal of Chemistry, 2005, pp. 291-305, vol. 29, XP002660686.

Extended European Search Report of EP11 17 2278, completion date Oct. 17, 2011.

* cited by examiner

*Primary Examiner* — Paul A Zucker
(74) *Attorney, Agent, or Firm* — Westerman, Hattori, Daniels & Adrian, LLP

(57) ABSTRACT

A rare earth metal extractant in the form of a dialkyl diglycol amic acid is synthesized by reacting diglycolic anhydride with a dialkylamine in an aprotic polar solvent, with a molar ratio of dialkylamine to diglycolic anhydride being at least 1.0, and removing the aprotic polar solvent.

16 Claims, 2 Drawing Sheets

SYNTHESIS OF RARE EARTH METAL EXTRACTANT

CROSS-REFERENCE TO RELATED APPLICATION

This non-provisional application claims priority under 35 U.S.C. §119(a) on Patent Application No. 2010-153175 filed in Japan on Jul. 5, 2010, the entire contents of which are hereby incorporated by reference.

TECHNICAL FIELD

This invention relates to a method for synthesizing an extractant for extracting and separating a selected rare earth element from a mixture of rare earth elements, specifically from a mixture of at least two light rare earth elements (La, Ce, Pr, Nd, Sm, and Eu) or from a mixture of at least one light rare earth element and at least one other rare earth element inclusive of yttrium.

BACKGROUND ART

In the modern society, rare earth elements are used in a wide variety of applications, for example, as rare earth magnets, phosphors, and electronic and electric materials in nickel hydrogen batteries. With respect to the supply of rare earth elements, a crisis of the rare earth resource is highlighted because the producers are limited, the price lacks stability, and the demand is expected to surpass the supply in the near future. For these reasons, many attempts are made to reduce the amount of rare earth element used and to develop a replacement. At the same time, it is desired to establish a recycle system for recovering rare earth elements as one valuable from in-process scraps produced during manufacture of products and municipal wastes like electric and electronic appliances collected from cities. Also there is an urgent need for the research and development of new rare earth mines.

Known methods for separating rare earth elements include column extraction (or solid to liquid extraction) using ion exchange resins, and solvent extraction (or liquid to liquid extraction). Although the column extraction (or solid to liquid extraction) method is simple in apparatus and easy in operation as compared with the solvent extraction, it is small in extraction capacity and discourages rapid treatment. The column extraction method is thus used in the removal of a metal when the concentration of a metal to be extracted in a solution is low, that is, when the metal to be extracted is present as an impurity, as well as in the waste water treatment. On the other hand, the solvent extraction (or liquid to liquid extraction) method needs a complex apparatus and cumbersome operation as compared with the column extraction, but provides for a large extraction capacity and rapid treatment. The solvent extraction method is thus used in industrial separation and purification of metal elements. For the separation and purification of rare earth elements that requires efficient treatment of a large volume through continuous steps, the solvent extraction method capable of such efficient treatment is often used.

In the solvent extraction method, an aqueous phase consisting of an aqueous solution containing metal elements to be separated is contacted with an organic phase consisting of an extractant for extracting a selected metal element and an organic solvent for diluting the extractant. Then the metal element is extracted with the extractant for separation.

Known extractants used in the art include tributyl phosphate (TBP), carboxylic acids (e.g., Versatic Acid 10), phosphoric acid esters, phosphonic acid compounds, and phosphinic acid compounds. These extractants are commercially available. A typical phosphoric acid ester is di-2-ethylhexylphosphoric acid (D2EHPA), a typical phosphonic acid compound is 2-ethylhexylphosphonic acid-mono-2-ethylhexyl ester (PC-88A by Daihachi Chemical Industry Co., Ltd.), and a typical phosphinic acid compound is bis(2,4,4 trimethylpentyl)phosphinic acid (Cyanex 272 by Cytec Industries).

The separation efficiency of the solvent extraction method depends on a separation ability of the metal extractant, specifically a separation factor. As the separation factor is higher, the separation efficiency of the solvent extraction method is higher, which enables simplification of separating steps and scale-down of the separation apparatus, making the process efficient and eventually leading to a cost reduction. A low separation factor, on the other hand, makes the separation process complex and poses a need for a large-scale separation apparatus.

Even PC-88A which is known to have a high separation factor for rare earth elements among the currently commercially available extractants has a low separation factor between elements of close atomic numbers, for example, a separation factor of less than 2, specifically about 1.4 between neodymium and praseodymium which are allegedly most difficult to separate among rare earth elements. The separation factor of this value is not sufficient for separation between neodymium and praseodymium. To separate them at an acceptable purity, a large-scale apparatus must be installed at the expense of cost. For more efficient separation of these elements, there is a desire for the development of an extractant having a higher separation factor than in the prior art and an extracting/separating method using the same.

Dialkyl diglycol amic acids are known from JP-A 2007-327085 as the metal extractant having a high separation factor with respect to rare earth elements, specifically light rare earth elements such as lanthanum (La), cerium (Ce), praseodymium (Pr), neodymium (Nd), and samarium (Sm). Using this extractant in solvent extraction, the extraction/separation step of rare earth elements, specifically light rare earth elements can be made more efficient. In fact, better results are obtained from the extraction/separation step of light rare earth elements using dialkyl diglycol amic acid on a laboratory scale.

When dialkyl diglycol amic acid was used as the metal extractant, satisfactory results were confirmed in a light rare earth element extraction/separation experiment which was conducted at a rare earth element concentration ($C_A$: 0.01 mol/L≤$C_A$≤0.7 mol/L) and a corresponding metal extractant concentration ($C_O$: 0.1 mol/L≤$C_O$≤1.5 mol/L) which were practical operating conditions of the rare earth element separating process and in a light rare earth element extraction/separation experiment using a countercurrent flow multistage mixer/settler of a practically operating apparatus.

The dialkyl diglycol amic acid exhibits a satisfactory separation factor in its performance as the metal extractant for separating light rare earth elements, as mentioned above, and its operating conditions have been surveyed. However, its synthesis has not been fully established.

The known method for synthesizing the dialkyl diglycol amic acid is in accord with the following reaction scheme.

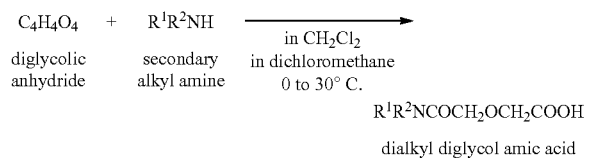

$R^1R^2NCOCH_2OCH_2COOH$ dialkyl diglycol amic acid

Herein $R^1$ and $R^2$ are each independently alkyl, and at least one is a straight or branched alkyl group of at least 6 carbon atoms.

First, diglycolic anhydride is suspended in dichloromethane. A secondary alkylamine in an amount slightly less than an equimolar amount to the diglycolic anhydride is dissolved in dichloromethane and the resulting solution is mixed with the suspension at 0 to 30° C. As diglycolic anhydride reacts, the mixed solution becomes clear. The reaction is completed when the solution becomes clear. This is followed by removal of water-soluble impurities by washing with deionized water, removal of water with a dehydrating agent (e.g., sodium sulfate), filtration, and solvent removal. Recrystallization from hexane is repeated plural times for purification, yielding the desired product (see JP-A 2007-327085).

This synthesis method uses as the synthesis medium dichloromethane which is one of the harmful substances listed in several environmental pollution control laws, regulations and Pollutant Release and Transfer Register (PRTR) in Japan and the corresponding regulations in many countries. It is recommended to avoid the substance. In addition, since the solubility of the reactant, diglycolic anhydride in dichloromethane is low, the synthesis reaction becomes solid-liquid reaction indicating poor reactivity.

The above synthesis method allegedly gives a yield of more than 90% because it is conducted only on a laboratory scale where the amount of synthesis is several grams. However, a prominent drop of yield occurs when the synthesis is enlarged to a scale of several kilograms or more. In fact, in a synthesis experiment conducted on a scale of several hundreds of grams, the yield decreases below 80%. Such a yield drop is unwanted.

CITATION LIST

Patent Document 1: JP-A 2007-327085

SUMMARY OF INVENTION

An object of the invention is to provide a method for synthesizing a rare earth metal extractant through efficient steps in improved yields without a need for dichloromethane which is used as reaction medium in the prior art synthesis.

The inventors have found that in the synthesis of a dialkyl diglycol amic acid serving as a rare earth metal extractant, better results are obtained by reacting reactants, diglycolic anhydride and a dialkylamine in an aprotic polar solvent as synthesis medium, and removing the synthesis medium. This method permits the dialkyl diglycol amic acid to be effectively synthesized in high yields.

The invention provides a method for synthesizing a rare earth metal extractant in the form of a dialkyl diglycol amic acid having the general formula (1):

wherein $R^1$ and $R^2$ are each independently alkyl, at least one being a straight or branched alkyl group of at least 6 carbon atoms, comprising the steps of reacting diglycolic anhydride with a dialkylamine in an aprotic polar solvent, with a molar ratio (B/A) of dialkylamine (B) to diglycolic anhydride (A) being at least 1.0, and removing the aprotic polar solvent.

The aprotic polar solvent is typically selected from among acetone, acetonitrile, tetrahydrofuran, N,N-dimethylformamide, and dimethyl sulfoxide.

In the reacting step, the molar ratio (B/A) of dialkylamine (B) to diglycolic anhydride (A) is preferably in a range of 1.0 to 1.2.

Advantageous Effects of Invention

According to the method of the invention, a dialkyl diglycol amic acid which is an extractant having an improved separation factor for light rare earth elements can be effectively synthesized in high yields without a need for a harmful solvent, dichloromethane. The method is of great worth in the industry.

DESCRIPTION OF EMBODIMENTS

Figure 1:
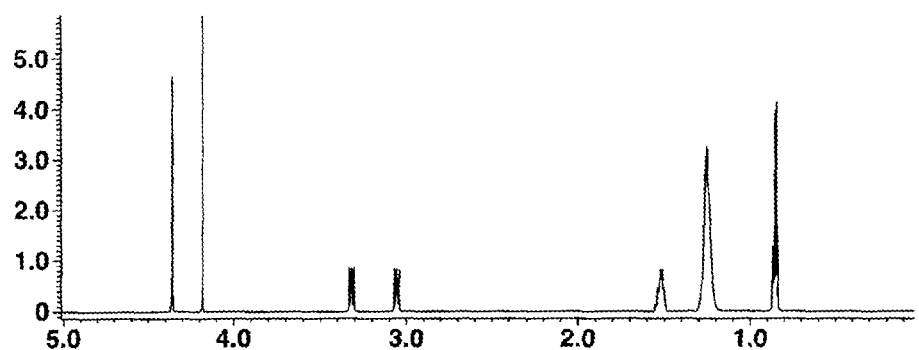
FIG. 1 is a $^1$H-NMR chart of the reaction product of Example 1.

The invention pertains to a rare earth metal extractant which is a dialkyl diglycol amic acid having the general formula (1).

Herein $R^1$ and $R^2$ are each independently alkyl, at least one of $R^1$ and $R^2$ being a straight or branched alkyl group of at least 6 carbon atoms, preferably 6 to 18 carbon atoms, and more preferably 7 to 12 carbon atoms. If the carbon count is less than 6, the compound failing to play the role of extractant because it is less lipophilic so that the organic phase lacks stability and exhibits poor separation from the aqueous phase, and because the dissolution of the extractant itself in aqueous phase becomes noticeable. An excessive carbon count contributes to no improvements in basic abilities like extraction and separation abilities despite the increased cost of extractant manufacture. As long as lipophilic nature is ensured, if one of $R^1$ and $R^2$ has a carbon count of at least 6, then the other may be of less than 6 carbon atoms. For example, a compound of formula (1) wherein two octyl ($-C_8H_{17}$) groups are introduced is most preferred, which is named N,N-dioctyl-3-oxapentane-1,5-amic acid or dioctyl diglycol amic acid (abbreviated as DODGAA, hereinafter).

According to the invention, the dialkyl diglycol amic acid is synthesized by reacting diglycolic anhydride with a dialkylamine in an aprotic polar solvent. The reactants used are diglycolic anhydride and a dialkylamine, which are dissolved in an aprotic polar solvent as synthesis medium and mixed together for reaction to take place. Thereafter, the aprotic polar solvent is removed by distilling off under atmospheric or subatmospheric pressure whereupon the desired dialkyl diglycol amic acid is obtainable. The dialkylamine used herein is a secondary alkylamine having alkyl groups corresponding to $R^1$ and $R^2$ in the dialkyl diglycol amic acid of formula (1).

The aprotic polar solvent used herein as synthesis medium refers to a solvent having amphiphatic nature, that is, both hydrophilic and lipophilic natures. Suitable solvents include acetone, acetonitrile, tetrahydrofuran (THF), N,N-dimethylformamide (DMF), and dimethyl sulfoxide (DMSO). Inter alia, acetone and THF are preferred from the standpoints of solvent removal in the synthesis process and the restriction on solvents by the PRTR and other regulations. The use of an aprotic polar solvent as synthesis medium has the advantage that since both the reactants, diglycolic anhydride and dialkylamine readily dissolve in the medium, the synthesis reaction becomes a liquid-liquid reaction, leading to improved reactivity.

If a non-polar solvent is used as synthesis medium, the dialkylamine having lipophilic nature readily dissolves in the medium, but diglycolic anhydride having hydrophilic nature has a low solubility in the medium. As a result, the synthesis reaction becomes a solid-liquid reaction, leading to low reactivity.

If a protic polar solvent is used as synthesis medium, the solubilities of diglycolic anhydride and dialkylamine in the solvent differ with the type of solvent. For example, where the synthesis medium is water, diglycolic anhydride readily dissolves therein, but ceases to be anhydride, retarding its reaction with dialkylamine. Where the synthesis medium is an alcohol, dialkylamine readily dissolves therein, but the solubility of diglycolic anhydride in alcohol is low. As a result, the synthesis reaction becomes a solid-liquid reaction, leading to low reactivity. In addition, part of diglycolic anhydride can form an alkyl ester with the alcohol. Then the diglycolic acid alkyl ester is left as an impurity, and the amount of dialkyl diglycol amic acid resulting from reaction is accordingly reduced. Furthermore, from the reaction, not only the desired dialkyl diglycol amic acid is obtainable, but an alkyl ester of dialkyl diglycol amic acid is also formed as byproduct. Since the diglycolic acid alkyl ester and the alkyl ester of dialkyl diglycol amic acid form complexes with rare earth metal ions, they have some rare earth metal extracting ability, but little separating ability, becoming an inhibitory factor to the extraction and separation in the solvent extraction process. The resulting reaction product is outstandingly poor in the ability of rare earth metal extractant to separate rare earth elements, as compared with the dialkyl diglycol amic acid.

In the prior art synthesis method, once the reaction is driven to completion, post-treatments including removal of water-soluble impurities by washing with deionized water, removal of water with a dehydrating agent, filtration of reaction solution, solvent removal, and repetition of recrystallization from hexane for purification are introduced until the desired product is obtained. In the synthesis method of the invention, once the reaction is driven to completion, the desired product can be recovered merely by removing the solvent without a need for post-treatment, although it is acceptable to carry out post-treatments including removal of water-soluble impurities by washing with deionized water, removal of water with a dehydrating agent, filtration of reaction solution, and recrystallization. The synthesis reaction according to the invention is a liquid-liquid reaction rather than solid-liquid reaction, offering a sufficient reactivity to eliminate a need to remove impurities by washing, recrystallization and the like.

In the reaction step, an amount (B mol) of dialkylamine and an amount (A mol) of diglycolic anhydride are used in a molar ratio (B/A) of at least 1.0, preferably $1.0 \leq B/A \leq 1.2$, and more preferably $1.0 \leq B/A \leq 1.1$. The resulting reaction product contains unreacted dialkylamine as well as the desired dialkyl diglycol amic acid. In the prior art method, plural times of recrystallization are necessary to remove the unreacted dialkylamine. It has been found that when solvent extraction is carried out using dialkyl diglycol amic acid having dialkylamine left therein, no problems arise with respect to separation efficiency and phase separation, ensuring effective extraction and separation. Specifically, even if the dialkylamine is left in the metal extractant and the organic phase during solvent extraction, it does not become an inhibitory factor to extraction and separation and there is no need to remove it as an impurity. As a result, the synthesis process can be simplified. A loss of the reaction product by recrystallization is minimized. These contribute to improved yields.

If $B/A > 1.2$, the resulting reaction product may contain an excess of unreacted dialkylamine as well as the desired dialkyl diglycol amic acid. This reaction product may be used as the extractant because no problems arise with respect to separation efficiency and phase separation during solvent extraction. However, use of excess dialkylamine is meaningless. Also the cost of reactants for synthesis increases, rendering the method less cost effective.

If $B/A < 1.0$, which means an excess of diglycolic anhydride for reaction, the desired dialkyl diglycol amic acid is obtained as the reaction product, in which unreacted diglycolic acid may remain. When solvent extraction is carried out using dialkyl diglycol amic acid having diglycolic acid left therein, no satisfactory separation ability is available and the solution becomes white turbid because clad is formed between organic phase and aqueous phase. This results in poor phase separation, failing in normal extraction and separation. This is because the diglycolic acid remaining along with the metal extractant, dialkyl diglycol amic acid forms a complex with a rare earth metal ion, inhibiting satisfactory extraction and separation. That is, diglycolic acid becomes an inhibitory factor to extraction. To obtain diglycolic acid-free dialkyl diglycol amic acid as the rare earth metal extractant capable of normal extraction and separation, the step of removing unreacted diglycolic acid is necessary as in the prior art method. Specifically, the water-soluble diglycolic acid must be removed by removing the synthesis medium and washing the reaction product with water. Upon water washing, however, the dialkyl diglycol amic acid having a very low solubility in water crystallizes and precipitates in the solvent (for example, a solubility of DODGAA in water is $6.2 \times 10^{-6}$ mol/L). In order to use the dialkyl diglycol amic acid in crystallized form as the rare earth metal extractant, filtration and drying steps are needed. The process becomes less efficient because extra steps are necessary as compared with the range of $1.0 \leq B/A \leq 1.2$.

EXAMPLE

Examples are given below by way of illustration and not by way of limitation.

Example 1 and Comparative Example 1

Synthesis of Rare Earth Metal Extractant and Extraction/Separation Test

DODGAA was synthesized using different synthesis media. The DODGAA products thus synthesized were examined for an ability to separate rare earth metals from a mixture thereof by the solvent extraction method.

First, 34.8 g (0.3 mol) of diglycolic anhydride was dissolved in 400 mL of acetone as synthesis medium. Separately, 72.4 g (0.3 mol) of dioctylamine was dissolved in 100 mL of acetone. With stirring, the dioctylamine solution was added dropwise to the diglycolic anhydride solution. Stirring was continued at room temperature until it was confirmed that the solution became clear as a result of reaction of diglycolic anhydride. Thereafter, acetone was removed by vacuum drying, yielding 105.2 g of the reaction product (Example 1).

In Comparative Example 1, the same procedure as above was repeated aside from using hexanol, a protic polar solvent, as the reaction solvent. The reaction product was obtained in an amount of 103.3 g.

Figure 2:
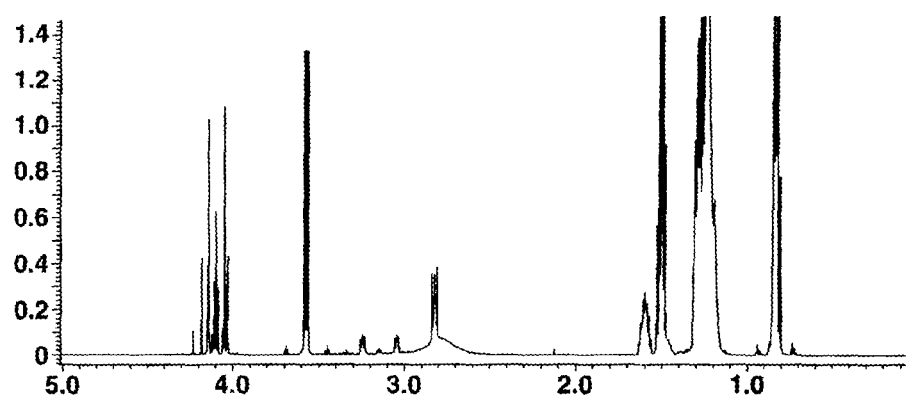
FIG. 2 is a $^1$H-NMR chart of the reaction product of Comparative Example 1.

The reaction products in Example 1 and Comparative Example 1 were analyzed by $^1$H-NMR spectroscopy as shown in FIGS. 1 and 2, respectively. The reaction product in Example 1 was identified to be DODGAA, while the reaction product in Comparative Example 1 was identified to be a mixture of DODGAA and the hexyl ester of DODGAA.

An extraction/separation test was performed by dissolving a portion of the reaction product in Example 1 or Comparative Example 1 in hexanol to form an organic solution having a concentration of 0.3 mol/L, which might become an organic phase.

An aqueous solution containing mixed rare earth metals was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted into the organic phase was back-extracted into the aqueous hydrochloric acid solution. The concentrations of praseodymium and neodymium in the aqueous phase and the back-extracted aqueous hydrochloric acid solution were measured by an ICP atomic emission spectrometer ICP-7500 (Shimadzu Corp.).

The results are reported as Nd/Pr separation factor in Table 1. The percent yield of the reaction product in Example 1 or Comparative Example 1 was computed from the total amount of the reactants, diglycolic anhydride and dioctylamine and the amount of the reaction product and also shown in Table 1.

Comparative Example 2

Diglycolic anhydride, 34.8 g (0.3 mol), was suspended in 400 mL of dichloromethane. Separately, 72.4 g (0.3 mol) of dioctylamine was dissolved in 100 mL of dichloromethane. With stirring, the dioctylamine solution was added dropwise to the diglycolic anhydride suspension. Stirring was continued at room temperature until it was confirmed that the solution became clear as a result of reaction of diglycolic anhydride. Thereafter, the reaction solution was washed with deionized water to remove the water-soluble impurities, dried over sodium sulfate as a dehydrating agent, filtered, and vacuum dried to remove the dichloromethane. Recrystallization was effected three times using 700 mL of n-hexane, obtaining 85.4 g of the reaction product.

Figure 3:
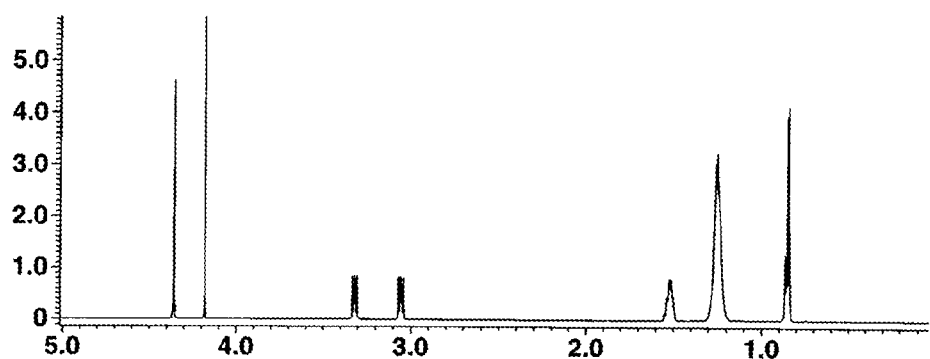
FIG. 3 is a $^1$H-NMR chart of the reaction product of Comparative Example 2.

The reaction product in Comparative Example 2 was analyzed by $^1$H-NMR spectroscopy as shown in FIG. 3. It was identified to be DODGAA.

Using the reaction product in Comparative Example 2, an extraction/separation test was performed under the same conditions as in Example 1.

The results are reported as Nd/Pr separation factor in Table 1. The percent yield of the reaction product in Comparative Example 2 was computed from the total amount of the reactants, diglycolic anhydride and dioctylamine and the amount of the reaction product and also shown in Table 1.

TABLE 1

|  | Synthesis medium | Yield | Nd/Pr separation factor |
|---|---|---|---|
| Example 1 | acetone | 98.1% | 2.5 |
| Comparative Example 1 | hexanol | 96.3% | 1.3 |
| Comparative Example 2 | dichloromethane | 79.6% | 2.5 |

The DODGAA obtained by the synthesis method of Example 1 showed a high yield while its Nd/Pr separation factor indicative of the separation ability as a metal extractant was satisfactory. The DODGAA obtained by the synthesis method of Comparative Example 1 showed a high yield, but its Nd/Pr separation factor was low because the hexyl ester of DODGAA became an inhibitory factor to rare earth metal separation. The DODGAA obtained by the synthesis method of Comparative Example 2 had a satisfactory Nd/Pr separation factor, but its yield was very low as compared with Example 1.

Examples 2 to 5 and Comparative Example 3

An amount (designated A in Table 2) of diglycolic anhydride was dissolved in 40 mL of acetone. Separately, an amount (designated B in Table 2) of dioctylamine was dissolved in 10 mL of acetone. With stirring, the dioctylamine solution was added dropwise to the diglycolic anhydride solution. Stirring was continued at room temperature until it was confirmed that the solution became clear as a result of reaction of diglycolic anhydride. Table 2 also reports a ratio B/A that is a ratio of the amount (B mmol) of dioctylamine to the amount (A mmol) of diglycolic anhydride. Thereafter, acetone was removed by vacuum drying, yielding the reaction product. The reaction products were analyzed by $^1$H-NMR spectroscopy, with DODGAA detected in all the products. A minor amount of dioctylamine was detected in Examples 2, 3 and 5 while a minor amount of diglycolic acid detected in Comparative Example 3.

An extraction/separation test was performed by dissolving a portion of each reaction product in Examples 2 to 5 and Comparative Example 3 in hexanol to form an organic solution having a concentration of 0.3 mol/L, which might become an organic phase.

An aqueous solution containing mixed rare earth metals was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted into the organic phase was back-extracted into the aqueous hydrochloric acid solution. The concentrations of praseodymium and neodymium in the aqueous phase and the back-extracted aqueous hydrochloric acid solution were measured by an ICP atomic emission spectrometer ICP-7500 (Shimadzu Corp.).

The extractant state, Nd/Pr separation factor, and phase separation are reported in Table 2.

TABLE 2

| | A diglycolic anhydride | | B dioctylamine | | | Extractant state | Nd/Pr separation factor | Phase separation |
|---|---|---|---|---|---|---|---|---|
| | (g) | (mmol) | (g) | (mmol) | B/A | | | |
| Example 2 | 3.5 | 30.2 | 8.4 | 34.8 | 1.15 | liquid | 2.5 | definite |
| Example 3 | 3.5 | 30.2 | 8.0 | 33.1 | 1.10 | liquid | 2.5 | definite |
| Example 4 | 3.5 | 30.2 | 7.3 | 30.2 | 1.00 | liquid | 2.5 | definite |
| Example 5 | 3.5 | 30.2 | 9.0 | 37.3 | 1.24 | solid | 2.5 | definite |
| Comparative Example 3 | 3.9 | 33.6 | 7.3 | 30.2 | 0.90 | liquid | — | indefinite |

In Examples 2, 3 and 4 wherein a ratio of the amount (B mmol) of dioctylamine to the amount (A mmol) of diglycolic anhydride is 1.0≤B/A≤1.2, the DODGAA's were obtained in high yields while their Nd/Pr separation factor indicative of the separation ability of a metal extractant and the phase separation were satisfactory.

In Example 5 wherein B/A>1.2, the Nd/Pr separation factor and the phase separation were satisfactory, but the reaction product was difficult to handle as compared with the other products because the excess dioctylamine in the reaction product solidified. In Comparative Example 3, the excess diglycolic anhydride became an inhibitory factor to extraction, causing indefinite phase separation, and the Nd/Pr separation factor could not be measured.

Japanese Patent Application No. 2010-153175 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for synthesizing a rare earth metal extractant in the form of a dialkyl diglycol amic acid having the general formula (I):

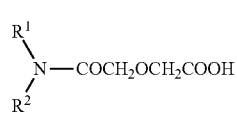

(1)

wherein $R^1$ and $R^2$ are each independently a straight or branched alkyl group of 6 to 18 carbon atoms, comprising the steps of:
reacting diglycolic anhydride with a dialkylamine in an aprotic polar solvent selected from the group consisting of acetone and acetonitrile, with a molar ratio (B/A) of dialkylamine (B) to diglycolic anhydride (A) being in a range of 1.0 to 1.2, and
removing the aprotic polar solvent.

2. The method of claim 1 wherein in the reacting step, the molar ratio (B/A) of dialkylamine (B) to diglycolic anhydride (A) is in a range of 1.0 to 1.1.

3. The method of claim 1 wherein the aprotic polar solvent comprises acetone.

4. The method of claim 1 comprising the step of mixing the diglycolic anhydride dissolved in the aprotic polar solvent with the dialkylamine dissolved in the aprotic polar solvent, prior to said reacting step.

5. The method of claim 1 wherein the aprotic polar solvent comprises acetone or acetonitrile.

6. A method for synthesizing a rare earth metal extractant in the form of a dialkyl diglycol amic acid having the general formula (I):

(1)

wherein $R^1$ and $R^2$ are each independently a straight or branched alkyl group of 6 to 18 carbon atoms, comprising the steps of:
reacting diglycolic anhydride with a dialkylamine in acetone, with a molar ratio (B/A) of dialkylamine (B) to diglycolic anhydride (A) being in a range of 1.0 to 1.2, and
removing the aprotic polar solvent.

7. The method of claim 6 wherein in the reacting step, the molar ratio (B/A) of dialkylamine (B) to diglycolic anhydride (A) is in a range of 1.0 to 1.1.

8. The method of claim 6 comprising the step of mixing the diglycolic anhydride dissolved in acetone with the dialkylamine dissolved in acetone, prior to said reacting step.

9. The method of claim 1 wherein $R^1$ and $R^2$ are each independently straight or branched alkyl group of 6 to 11 carbon atoms.

10. The method of claim 1 wherein $R^1$ and $R^2$ are each respectively straight or branched alkyl group represented by $C_8H_{17}$—.

11. The method of claim 2 wherein $R^1$ and $R^2$ are each independently straight or branched alkyl group of 6 to 11 carbon atoms.

12. The method of claim 2 wherein $R^1$ and $R^2$ are each respectively straight or branched alkyl group represented by $C_8H_{17}$—.

13. The method of claim 6 wherein $R^1$ and $R^2$ are each independently straight or branched alkyl group of 6 to 11 carbon atoms.

14. The method of claim 6 wherein $R^1$ and $R^2$ are each respectively straight or branched alkyl group represented by $C_8H_{17}-$.

15. The method of claim 7 wherein $R^1$ and $R^2$ are each independently straight or branched alkyl group of 6 to 11 carbon atoms.

16. The method of claim 7 wherein $R^1$ and $R^2$ are each respectively straight or branched alkyl group represented by $C_8H_{17}-$.

* * * * *